(12) United States Patent
Bergeron et al.

(10) Patent No.: US 6,300,296 B1
(45) Date of Patent: Oct. 9, 2001

(54) FOAMING AQUEOUS MEDIUM STABLE IN THE PRESENCE OF GREASE, STABILIZATION OF A FOAMING AQUEOUS MEDIUM IN THE PRESENCE OF GREASE

(75) Inventors: Vance Bergeron, Lyons; Gilles Guerin, Eaubonne, both of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/355,485

(22) PCT Filed: Jan. 30, 1998

(86) PCT No.: PCT/FR98/00173

§ 371 Date: Oct. 5, 1999

§ 102(e) Date: Oct. 5, 1999

(87) PCT Pub. No.: WO98/33877

PCT Pub. Date: Aug. 6, 1998

(30) Foreign Application Priority Data

Jan. 31, 1997 (FR) .................................................. 97 01049

(51) Int. Cl.$^7$ .............................. A61K 7/075; A61K 7/50; B01F 17/02; C11D 3/24
(52) U.S. Cl. ..................... 510/127; 424/70.19; 510/135; 510/235; 510/341; 514/945; 514/975; 516/12
(58) Field of Search ............................... 516/12; 510/135, 510/158, 221, 341, 405, 127, 235; 424/70.19; 514/945, 975

(56) References Cited

U.S. PATENT DOCUMENTS

| | | |
|---|---|---|
| 3,194,767 | 7/1965 | Berry . |
| 4,089,804 * | 5/1978 | Falk .................................... 516/12 X |
| 4,130,497 * | 12/1978 | Oneto et al. ...................... 510/158 X |
| 4,306,997 * | 12/1981 | Oneto et al. .......................... 510/135 |
| 4,713,182 * | 12/1987 | Hiltz et al. .......................... 516/12 X |
| 4,765,975 * | 8/1988 | Iovanni et al. ..................... 424/70.19 |
| 5,085,786 * | 2/1992 | Alm et al. ........................... 516/12 X |
| 5,093,023 * | 3/1992 | Pantini et al. .................... 510/135 X |
| 5,561,106 * | 10/1996 | Erilli et al. ........................ 510/405 X |
| 5,767,054 * | 6/1998 | Sprugel et al. ................... 510/405 X |
| 5,922,662 * | 7/1999 | Thomas ............................. 510/405 X |
| 5,980,876 * | 11/1999 | Peffly ............................ 424/70.19 X |

FOREIGN PATENT DOCUMENTS

| | | |
|---|---|---|
| 22 40 263 | 2/1973 | (DE) . |
| 96 31187 | 10/1996 | (WO) . |

OTHER PUBLICATIONS

Database WPI, Section Ch, Week 8107, Derwent Publications Ltd., London, GB, AN 81–10607D, XP002043770 & JP 55 157 691 A (Sanyo Chem Ind Ltd), Dec. 8, 1980.
Database WPI, Section Ch, Week 8030, Derwent Publications Ltd., London, GB; AN 80–52100C XP002043771 & JP 55 075 498 A (Sanyo Chem Ind Ltd), Jun. 6, 1980.

* cited by examiner

Primary Examiner—Richard D. Lovering
(74) Attorney, Agent, or Firm—Burns, Doane, Swecker & Mathis, L.L.P.

(57) ABSTRACT

The invention concerns a foaming aqueous medium (FAM) capable of forming a stable foam in the presence of grease (G). The foaming aqueous medium (FAM) of the present invention comprises water, at least one base surface-active agent (BSA) which comprises at least one amphiphilic additive (ADD), which is a fluorinated compound, compatible with said base surface-active agent (BSA). The present invention further concerns a liquid detergent composition for washing dishes by hand or textiles by hand comprising an effective amount of the foaming aqueous medium (FAM) of the present invention. The present invention also concerns a liquid composition for body hygiene, oral hygiene or body treatment comprising an effective amount of the foaming aqueous medium (FAM) of the present invention.

2 Claims, No Drawings

FOAMING AQUEOUS MEDIUM STABLE IN THE PRESENCE OF GREASE, STABILIZATION OF A FOAMING AQUEOUS MEDIUM IN THE PRESENCE OF GREASE

This application is a 371 of PCT/FR98/00173, filed on Jan. 30, 1998.

The subject-matter of the present invention is a foaming aqueous medium which can form foams which remain stable in the presence of grease, the stabilization of the foams, in the presence of grease, of an aqueous medium comprising a base surface-active agent using an amphiphilic additive, and the use of the said aqueous medium which can form foams which remain stable in the presence of grease as liquid detergent composition for washing dishes by hand, as liquid cosmetic composition for the skin or hair, such as shampoos., shower gels or liquid soaps, as composition for the floating of metals, and the like.

Various types of additives have already been provided for stabilizing foams resulting from aqueous media comprising a surface-active agent, in particular in the field of detergency. The following are in particular mentioned in "Additives for foams", Kuo-Yann Lai and Nagaraj Dixit, Foams theory measurements and applications; edited by Robert K. Prud'homme and Saad A. Khan; Surfactant Science series—volume 57, Marcel Dekker Inc., 1995, chapter 8:

organic compounds, such as fatty alcohols, such as lauryl alcohol, for improving the stability of aqueous media comprising an anionic surfactant, such as alkyl sulfates or alkylsulfonates, or a nonionic surfactant, such as ethoxylated alcohols;

alkanolamides, such as lauryl monoethanolamide and lauryl isopropanolamide, for improving the stability of aqueous media comprising an anionic surfactant, such as alkylarylsulfonates;

amine oxides, such as N,N-dimethyldodecylamine or N,N-dimethylmyristylamine oxides, for improving the stability of aqueous media comprising an anionic surfactant, such as alkyl ether sulfates or alkylarylsulfonates;

electrolytes, such as disodium hydrogen phosphate, disodium pyrophosphate and pentasodium tripolyphosphate, for improving the stability of aqueous media comprising sodium laurate;

hydrophilic polymers, such as nonionic water-soluble derivatives of cellulose or of guar gum, for improving the stability of aqueous media comprising an anionic surfactant, such as alkyl sulfates, alkylethersulfonates or alkylsulfonates, a nonionic surfactant, such as ethoxylated alcohols, or an amphoteric surfactant, such as betaines.

However, these various additives exhibit the disadvantage of not always contributing, in the presence of grease, sufficient stability to the foams formed.

The Applicant Company has found a foaming aqueous medium, the foams of which exhibit a particularly improved stability in the presence of grease.

A first subject-matter of the present invention consists of a foaming aqueous medium (FAM) which can form stable foams in the presence of grease (G), the said foaming aqueous medium (FAM) comprising water and at least one base surface-active agent (BSA) which can disperse and/or dissolve the grease (G) in the water and being characterized in that it additionally comprises at least one amphiphilic additive (ADD) compatible with the said base surface-active agent (BSA), the said amphiphilic additive (ADD) exhibiting, at a concentration of 0.1% by weight in water, a surface tension $\gamma_{(ADD)\ water/air}$ of less than 25 mN/m, preferably of less than 22 mN/m, at 25° C. and exhibiting an affinity for the grease (G) which is less than that of the base surface-active agent (BSA) for the said grease (G).

The term "grease (G)" is understood to mean any liquid and/or solid hydrophobic hydrocarbon-comprising medium exhibiting, for example, a solubility in water of less than 5 g/l, preferably of less than 1 g/l.

This grease (G) can be contributed by the external environment and/or can be a constituent of the foaming aqueous medium (FAM) itself; thus, it can equally well be a hydrophobic stain and a hydrophobic active compound of a detergent or cosmetic formulation, for example. Mention may be made, by way of example of grease (G) of:

aliphatic or aromatic hydrocarbons (alkanes, paraffins, mineral oils, paraffin oils, kerosene, petroleum, fuel oil, perhydrosqualane, squalene, and the like), alkyl monoglycerides, alkyl diglycerides, triglycerides, such as oils extracted from plants and vegetables (palm oil, coconut oil, cottonseed oil, soybean oil, sunflower oil, olive oil, grape seed oil, sesame oil, groundnut oil, castor oil and the like) or oils of animal origin (tallow, fish oils, and the like), or derivatives of these oils, such as hydrogenated oils or lanolin derivatives, fatty alcohols, such as cetyl alcohol, stearyl alcohol or oleyl alcohol, fatty esters, such as isopropyl palmitate, 2-ethylhexyl cocoate, myristyl myristate or esters of lactic acid, of stearic acid, of behennic acid or of isostearic acid, polyorganosiloxane oils, gums or resins, such as linear or cyclic polydimethylsiloxanes, $\alpha,\omega$-hydroxylated polydimethylsiloxanes, $\alpha,\omega$-trimethylsilylated polydimethylsiloxanes, polyalkylmethylsiloxanes, polymethylphenylsiloxanes, polydiphenylsiloxanes, aminated derivatives of silicones, or silicone waxes, organic stains (sebum, and the like).

Any type of nonionic, anionic, amphoteric, zwitterionic or cationic surface-active agent can constitute the base surface-active agent(s) (BSA).

Mention may be made, among these surface-active agents, of anionic surface-active agents, such as alkyl ester sulfonates of formula R—CH(SO$_3$M)—COOR', where R represents a C$_{8-20}$, preferably C$_{10}$–C$_{16}$, alkyl radical, R' a C$_1$–C$_6$, preferably C$_1$–C$_3$, alkyl radical and M an alkali metal (sodium, potassium or lithium) cation, a substituted or unsubstituted ammonium (methyl-, dimethyl-, trimethyl- or tetramethylammonium, dimethylpiperidinium, and the like) cation or a cation derived from an alkanolamine (monoethanolamine, diethanolamine, triethanolamine, and the like);

alkyl sulfates of formula ROSO$_3$M, where R represents a C$_5$–C$_{24}$, preferably C$_{10}$–C$_{18}$, alkyl or hydroxyalkyl radical, M representing a hydrogen atom or a cation with the same definition as above, and their ethoxylenated (EO) and/or propoxylenated (PO) derivatives exhibiting an average of 0.5 to 30, preferably of 0.5 to 10, EO and/or PO units;

alkylamide sulfates of formula RCONHR'OSO$_3$M, where R represents a C$_2$–C$_{22}$, preferably C$_6$–C$_{20}$, alkyl radical, R' a C$_2$–C$_3$ alkyl radical, M representing a hydrogen atom or a cation with the same definition as above, and their ethoxylenated (EO) and/or propoxylenated (PO) derivatives exhibiting an average of 0.5 to 60 EO and/or PO units;

salts of $C_8$–$C_{24}$, preferably $C_{14}$–$C_{20}$, saturated or unsaturated fatty acids, $C_9$–$C_{20}$ alkylbenzenesulfonates, primary or secondary $C_8$–$C_{22}$ alkylsulfonates, alkylglycerol sulfonates, the sulfonated polycarboxylic acids disclosed in GB-A-1,082,179, paraffin sulfonates, N-acyl-N-alkyltaurates, alkyl phosphates, isethionates, alkylsuccinamates, alkylsulfosuccinates, the monoesters or diesters of sulfosuccinates, N-acylsarcosinates, alkylglycoside sulfates or polyethoxycarboxylates the cation being an alkali metal (sodium, potassium or lithium), a substituted or unsubstituted ammonium residue (methyl-, dimethyl-, trimethyl- or tetramethylammonium, dimethylpiperidinium, and the like), or a residue derived from an alkanolamine (monoethanolamine, diethanolamine, triethanolamine, and the like);

sophorolipids, such as those in acid or lactone form, derivatives of 17-hydroxyoctadecenoic acid; and the like nonionic surface-active agents, such as polyoxyalkylenated (polyethoxyethylenated, polyoxypropylenated or polyoxybutylenated)alkylphenols, the alkyl substituent of which is $C_6$–$C_{12}$, comprising from 5 to 25 oxyalkylene units; mention may be made, by way of example, of Triton X-45, X-114, X-100 or X-102, sold by Rohm & Haas Co., or Igepal NP2 to NP17 from Rhône-Poulenc;

polyoxyalkylenated $C_8$–$C_{22}$ aliphatic alcohols comprising from 1 to 25 oxyalkylene (oxyethylene or oxypropylene) units; mention may be made, by way of example, of Tergitol 15-S-9 or Tergitol 24-L-6 NMW, sold by Union Carbide Corp., Neodol 45-9, Neodol 23-65, Neodol 45-7 or Neodol 45-4, sold by Shell Chemical Co., Kyro EOB, sold by The Procter & Gamble Co., Synperonic A3 to A9 from ICI, or Rhodasurf IT, DB and B from Rhône-Poulenc;

the products resulting from the condensation of ethylene oxide or of propylene oxide with propylene glycol or ethylene glycol, with a weight molecular mass of the order of 2000 to 10,000, such as the Pluronics sold by BASF;

the products resulting from the condensation of ethylene oxide or of propylene oxide with ethylenediamine, such as the Tetronics sold by BASF; ethoxylated and/or propoxylated $C_8$–$C_{18}$ fatty acids comprising from 5 to 25 ethoxylated and/or propoxylated units;

$C_8$–$C_{20}$ fatty acid amides comprising from 5 to 30 ethoxylated units;

ethoxylated amines comprising from 5 to 30 ethoxylated units;

alkoxylated amidoamines comprising from 1 to 50, preferably from 1 to 25, very particularly from 2 to 20, oxyalkylene units (preferably oxyethylene units;

amine oxides, such as ($C_{10}$–$C_{18}$ alkyl)dimethylamine oxides or ($C_8$–$C_{22}$ alkoxy)ethyldihydroxyethylamine oxides;

alkoxylated terpene hydrocarbons, such as ethoxylated and/or propoxylated α- or β-pinenes, comprising from 1 to 30 oxyethylene and/or oxypropylene units;

the alkylpolyglycosides which can be obtained by condensation (for example by acid catalysis) of glucose with primary fatty alcohols (U.S. Pat. Nos. 3,598,865, 4,565,647, EP-A-132,043, EP-A-132,046, and the like) exhibiting a $C_4$–$C_{20}$, preferably $C_8$–$C_{18}$, alkyl group and a mean number of glucose units of the order [lacuna] 0.5 to 3, preferably of the order of 1.1 to 1.8, per mole of alkylpolyglycoside (APG); mention may in particular be made of those exhibiting a $C_8$–$C_{14}$ alkyl group and, on average, 1.4 glucose units per mole a $C_{12}$–$C_{14}$ alkyl group and, on average, 1.4 glucose units per mole a $C_8$–$C_{14}$ alkyl group and, on average, 1.5 glucose units per mole a $C_8$–$C_{10}$ alkyl group and, on average, 1.6 glucose units per mole sold respectively under the names Glucopon 600 EC®, Glucopon 600 CSUP®, Glucopon 650 EC® and Glucopon 225 CSUP® by Henkel;

glucosamides, such as lauryl-N-methylglucosamide;

cationic surface-active agents, such as primary, secondary or tertiary fatty amines (such as Armeen 12®, Armeen 2C®, Armeen DM12D® or Armeen M2HT®, sold by Armour)

fatty diamines (such as Duomeen C®, Duomeen CD® or Duomeen T®, sold by Armour)

primary or secondary fatty amine acetates (such as Armac C®, Armac 18D® or Armac T®, sold by Armour)

benzalkonium chloride quaternary ammonium halides (alkyldimethylammonium halides);

amphoteric and zwitterionic surface-active agents, such as alkyl betaines, alkyl dimethyl betaines, alkyl amidopropyldimethyl betaines, alkyl amidopropyl betaines, alkyl amidopropyldimethyl betaines, alkyl trimethyl sulfobetaines, imidazoline derivatives, such as alkylamphoacetates, alkylamphodiacetates, alkylamphopropionates or alkylamphodipropionates, alkyl sultaines or alkyl amidopropyl hydroxysultaines, the alkyl group of which comprises from 6 to 20 carbon atoms, the condensation products of fatty acids and of protein hydrolysates, or amphoteric derivatives of alkylpolyamines, such as Amphionic XL® or Mirataine H2C-HA®, which are sold by Rhône-Poulenc, Ampholac 7T/X® and Ampholac 7C/X®, which are sold by Berol Nobel.

The foam-stabilizing amphiphilic additive (ADD) can be foaming or nonfoaming.

The said amphiphilic additive (ADD) is preferably intrinsically foaming in the presence of water. This means that an aqueous solution (deionized water) comprising 0.1% by weight of the said additive (ADD) exhibits an initial foam height of at least 100 mm approximately at 41° C. according to the Ross-Miles foaming test (ASTM-D 1173-53).

The said additive (ADD) must exhibit an affinity for the grease (G) which is less than that of the base surface-active agent (BSA) for the grease (G). This condition is achieved when the addition of the said additive (ADD) to an aqueous solution of base surface-active agent (BSA) does not make it possible to modify by more than 5 mN/m, preferably not more than 3 mN/m, very particularly not more than 1 mN/m, the grease/aqueous solution of base surface-active agent (BSA) interfacial tension. This characteristic of the additive (ADD) can thus be written in the form $|\gamma_1 - \gamma_2| \leq 5$ mN/m preferably $|\gamma_1 - \gamma_2| \leq 3$ mN/m very particularly $|\gamma_1 - \gamma_2| \leq 1$ mN/m $\gamma_1$ representing the interfacial tension between the grease (G) and the aqueous solution of base surface-active agent (BSA) [(that is to say, without additive (ADD)]

$\gamma_2$ representing the interfacial tension between the grease (G) and the foaming aqueous medium (FAM) [(that is to say, comprising the additive (ADD)].

In addition, the amphiphilic additive (ADD) must be compatible with the base surfactant (BSA). This means that the presence of the said additive (ADD) does not lead to the destabilization of the solution of base surfactant (BSA) in water. Such a destabilization might be brought about by the presence in the said additive of ionic charges opposite to those of the base surface-active agent (BSA). Thus, it is advisable not to bring together, within the said foaming aqueous medium (FAM), a cationic additive and an anionic base surface-active agent, or vice versa.

In a very preferred way, the said additive (ADD) is a fluorinated compound.

Mention may be made, among fluorinated amphiphilic additives (ADD) which can be employed, of:

anionic, nonionic or amphoteric perfluoroalkylated surface-active agents exhibiting the above characteristics, such as
those of formula
$F(CF_2CF_2)_{3-8}CH_2CH_2SCH_2CH_2COOLi$
$F(CF_2CF_2)_{3-8}CH_2CH_2O(CH_2CH_2O)_yH$
$F(CF_2CF_2)_{3-8}CH_2CH_2SCH_2CH_2N^+(CH_3)_3CH_3SO_4^-$
$F(CF_2CF_2)_{3-8}CH_2CH(OCOCH_3)CH_2N^+(CH_3)_2$
$CH_2CH_2CO_2^-$ sold by du Pont de Nemours under the names Zonyl FSA, Zonyl FSO, Zonyl FSC and Zonyl FSK respectively;

perfluoroalkyl betaines, such as that sold by Elf Atochem under the name Forafac 1157, ethoxylated polyfluoroalcohols, such as that sold by Elf Atochem under the name Forafac 1110 D, or polyfluoroalkyl ammonium salts, such as that sold by Elf Atochem under the name Forafac 1179;

surface-active agents, the hydrophilic part of which comprises one or more saccharide unit(s) comprising from 5 to 6 carbon atoms (units derived from sugars, such as fructose, glucose, mannose, galactose, talose, gulose, allose, altose, idose, arabinose, xylose, lyxose and/or ribose) and the hydrophobic part of which comprises a unit of formula $R_F(CH_2)_n—$, where n can range from 2 to 20, preferably from 2 to 10, and $R_F$ represents a perfluoroalkyl unit of formula $C_mF_{2m+1}$ with m being able to range from 1 to 10, preferably from 4 to 8, which are chosen from those exhibiting the characteristics defined above; mention may be made of monoesters of perfluoroalkylated fatty acids and of sugars, such as α,α-trehalose and sucrose, it being possible for the monoester functional group to be represented by the formula $R_F(CH_2)_nC(O)$, where n can range from 2 to 10 and $R_F$ represents a perfluoroalkyl unit of formula $C_mF_{2m+1}$ with m being able to range from 4 to 8, which are described in JAOCS, vol. 69, No. 1 (January 1992) and are chosen from those exhibiting the characteristics defined above;

polyelectrolytes exhibiting fatty perfluoroalkyl side groups, such as polyacrylates exhibiting $R_F(CH_2)_n—$ groups, where n can range from 2 to 20, preferably from 2 to 10, and $R_F$ represents a perfluoroalkyl unit of formula $C_mF_{2m+1}$ with m being able to range from 1 to 10, preferably from 4 to 8, which are chosen from those exhibiting the characteristics defined above; mention may be made of polyacrylates exhibiting $—CH_2C_7F_{15}$ groups described in J. Chim. Phys. (1999), 93, 887–898 and which are chosen from those exhibiting the characteristics defined above.

The respective amounts of the various constituents of the said foaming aqueous medium (FAM) are such that the said foaming aqueous medium (FAM) comprises of the order of 0.1 to 10 g/l, preferably of the order of 0.3 to 5 g/l, very particularly of the order of 0.3 to 1.5 g/l, of base surfactant (BSA), expressed on a dry basis, the amphiphilic additive (ADD)/base surfactant (BSA) ratio by weight, each of these two being expressed on a dry basis, being of the order of 0.5/100 to 40/100, preferably of the order of The said foaming aqueous medium (FAM) can be prepared by a simple operation of mixing its various components in any order.

A second subject-matter of the invention consists of the use, in an aqueous medium comprising at least one base surface-active agent (BSA) which can disperse and/or dissolve grease (G) in water, of at least one amphiphilic additive (ADD) which is compatible with the said base surface-active agent (BSA), the said amphiphilic additive (ADD) exhibiting, at a concentration of 0.1% by weight in water, a surface tension $\gamma_{(ADD)\ water/air}$ of less than 25 mN/m, preferably of less than 22 mN/m, at 25° C. and exhibiting an affinity for the grease (G) which is less than that of the base surface-active agent (BSA) for the said grease (G).

The nature and relative amounts of base surface-active agent(s) (BSA) and of amphiphilic additive (ADD) present in the said aqueous medium have already been mentioned above.

A third subject-matter of the invention consists of a process for the stabilization of the foams in the presence of grease (G) of an aqueous medium comprising at least one base surface-active agent (BSA) by addition to the said aqueous medium of an amphiphilic additive (ADD) which is compatible with the said base surface-active agent (BSA), the said amphiphilic additive (ADD) exhibiting, at a concentration of 0.1% by weight in water, a surface tension $\gamma_{(ADD)\ water/air}$ of less than 25 mN/m, preferably of less than 22 mN/m, at 25° C. and exhibiting an affinity for the grease (G) which is less than that of the base surface-active agent (BSA) for the said grease (G).

The presence of the amphiphilic additive (ADD) in the foaming aqueous medium (FAM) makes it possible to obtain foaming performances (according to the test described in the example) at least equal to 20%, preferably at least equal to 80%, for a grease/[base surfactant (BSA)+amphiphilic additive (ADD)] ratio by weight of less than 40, preferably of less than 10.

The said foaming aqueous medium (FAM) forming the subject-matter of the invention which can form stable foams in the presence of grease (G) can be used in various applications requiring the use of a foaming medium with sufficient stability in the presence of grease (G).

The said medium (FAM) can be employed as liquid detergent composition for washing dishes by hand or textiles by hand. The medium can additionally comprise other components which are standard in this type of application, such as bactericidal or disinfecting agents, such as triclosan
  synthetic cationic polymers, such as Mirapol A550® or Mirapol A15®, which are sold by Rhône-Poulenc, Merquat 550®, sold by Calgon, and the like
  polymers used to control the viscosity of the mixture and/or the stability of the foams formed on use, such as derivatives of cellulose or of guar (carboxymethylcellulose, hydroxyethylcellulose, hydroxypropylguar, carboxymethylguar, carboxymethylhydroxypropylguar, and the like
  hydrotropic agents, such as short $C_2$–$C_8$ alcohols, in particular ethanol, diols and glycols, such as diethylene glycol or dipropylene glycol, and the like
  moisturizing or humectant agents for the skin, such as glycerol, urea or skin-protecting agents, such as proteins or protein hydrolysates, or cationic polymers, such as cationic derivatives of guar (Jaguar C13S®, Jaguar C162® or Hicare 1000®. sold by Rhône-Poulenc, colorants, fragrances, preservatives, and the like enzymes agents for complexing iron and bivalent ions in particular calcium or magnesium), such as aminocarboxylates, for example ethylenediaminetetraacetates, hydroxyethylethylenediaminetriacetates or nitrilotriacetates, aminophosphonates, such as nitrilotris (methylenephosphonates), or water-soluble salts of polycarboxylic acids with a molecular mass of the order of 2000 to 100,000, obtained by polymerization or copolymerization of ethylenically unsaturated carboxylic acids, such as acrylic acid, maleic acid or anhydride, fumaric acid, itaconic acid, aconitic acid, mesaconic acid, citraconic acid or methylenemalonic acid, and very particularly polyacrylates with a molecular mass of the order of 2000 to 10,000 (U.S. Pat. No. 3,308,067) or copolymers of acrylic acid and of maleic anhydride with a molecular mass of the order of 5000 to 75,000 (EP-A-66,915).

The said medium (FAM) can also be be employed as liquid composition for body hygiene, oral hygiene or body treatment (skin and hair), such as shampoos, shower gels, liquid soaps, shaving foams, depilatory foams, and the like), and can additionally comprise other components which are standard in these types of application.

The said aqueous medium (FAM) can thus comprise, in the fields of hair or skin hygiene or treatments, a supplementary vehicle, such as, in particular, ethanol or volatile silicones (such as phenylpentamethylsiloxane, methoxypropylheptamethylcyclotetrasiloxane, chloropropylpentamethyldisiloxane, hydropropylpentamethyldisiloxane, octamethylcyclotetrasiloxane, decamethylcyclopentasiloxane, cyclodimethicone and dimethicone);

a propellant, such as trichlorofluoromethane, dichlorodifluoromethane, difluoroethane, dimethyl ether, propane, n-butane or isobutane;

conditioning agents (which improve the combability, the styling, the feel and the body of the hair), such as conditioning agents of animal origin, for example animal protein hydrolysates, for example the salt of ammonium of dimethyl- or trimethyl stearate of collagen, silk or keratin hydrolysates; conditioning agents of synthetic origin, better known under the name polyquaternium, such as the copolymer of N,N'-bis(3-(dimethylamino)propyl)urea and of 1,1'-oxybis-(2-chloro)ethane or polyquaternium-2, or the copolymer of diallyldimethylammonium chloride and of acrylamide or polyquaternium-7; cationic derivatives of polysaccharides, such as cellulose cocodimonium hydroxyethyl, guar hydroxypropyl trimonium chloride, hydroxypropyl guar hydroxypropyl trimonium chloride (Jaguar C13S or Jaguar C162, sold by Rhône-Poulenc) or poly(oxyethane-1,2-diyl) 2-hydroxy chloride 3-(trimethylammonium)propyl cellulose ether or polyquaternium-10; silicone derivatives, such as amodimethicone, cyclomethicone, cetyl dimethicone copolyol, cyclomethicone, dimethicone copolyol, trimethylsilylamodimethicone or polyquaternium-80; or surface-active agents of cationic type, such as polyalkylammonium halides, for example distearyldimethylammonium chloride;

emollients, such as alkyl monoglycerides, alkyl diglycerides, triglycerides, such as oils extracted from plants and vegetables (palm oil, coconut oil, cottonseed oil, soybean oil, sunflower oil, olive oil, grape seed oil, sesame oil, groundnut oil, castor oil, and the like) or oils of animal origin (tallow, fish oils, and the like), derivatives of these oils, such as hydrogenated oils or lanolin derivatives, mineral oils or paraffin oils, perhydrosqualene, squalene, diols, such as 1-2-propanediol or 1-3-butanediol, cetyl alcohol, stearyl alcohol, oleyl alcohol, polyethylene glycols or polypropylene glycols, fatty esters, such as isopropyl palmitate, 2-ethylhexyl cocoate, myristyl myristate or esters of lactic acid, stearic acid, behennic acid or isostearic acid, silicone oils combining cyclic polydimethylsiloxanes, α,ω-hydroxylated polydimethylsiloxanes, α,ω-trimethylsilylated polydimethylsiloxanes, polyorganosiloxanes, such as polyalkylmethylsiloxanes, polymethylphenylsiloxanes, polydiphenylsiloxanes, aminated derivatives of silicones, silicone waxes, silcone copolyethers (such as the oil Silbione 70646, sold by the company Rhône-Poulenc, or DC 190, sold by Dow Corning) or the mixed derivatives of silicones, including various types of derivatization (such as the polyalkylmethylsiloxane-silicone copolyether mixed copolymers);

humectant or moisturizing agents, such as carbohydrates (glycerol or sorbitol, for example), polyethylene glycols or polypropylene glycols, alkoxylated derivatives of sugars or of their derivatives (methyl glucose, for example), urea, gelatin, aloe vera, hyaluronic acid, and the like protecting agents, such as polymeric derivatives of the cellulose derivatives type, such as cellulose hydroxyethers, methylcellulose, ethylcellulose, hydroxypropyl methylcellulose of hydroxybutyl methylcellulose, poly(vinyl ester)s grafted to polyalkylene backbones, such as poly(vinyl acetate)s grafted to polyoxyethylene backbones (EP-A-219,048), poly(vinyl alcohol)s, copolyesters derived from terephthalic and/or isophthalic and/or sulfoisophthalic acid or anhydride or from a terephthalic and/or isophthalic and/or sulfoisophthalic diester and from a diol, ethoxylated monoamines or polyamines, or polymers of ethoxylated amines (U.S. Pat. No. 4,597,898 and EP-A-11, 984)

plasticizers, such as adipates, phthalates, isophthalates, azelates, stearates, silicone copolyols, glycols, castor oil or their mixtures metal-sequestering agents, more particularly those sequestering calcium, such as citrate ions polymeric dispersants for controlling the calcium and magnesium hardness, agents such as water-soluble salts of polycarboxylic acids with a molecular mass of the order of 2000 to 100,000, obtained by polymerization or copolymerization of ethylenically unsaturated carboxylic acids, such as acrylic acid, maleic acid or anhydride, fumaric acid, itaconic acid, aconitic acid, mesaconic acid, citraconic acid or methylenemalonic acid, and very particularly polyacrylates with a molecular mass of the order of 2000 to 10,000 (U.S. Pat. No. 3,308,067), copolymers of acrylic acid and of maleic anhydride with a molecular mass of the order of 5000 to 75,000 (EP-A-66,915) or polyethylene glycols with a molecular mass of the order of 1000 to 50,000 viscosifying or gelling polymers, such as crosslinked polyacrylates (Carbopol, sold by Goodrich), cellulose derivatives, such as hydroxypropylcellulose or carboxymethylcellulose, guars and their derivatives, xanthan gum, and the like sunscreen agents, such as zinc oxide, titanium dioxide or cerium oxides in the powder form or in the form of colloidal particles preservatives, fragrances, colorants, and the like.

In the field of oral hygiene (dentifrices), the said aqueous medium (FAM) can comprise fluorinated compounds, such as salts of monofluorophosphoric acid, humectant agents, such as glycerol, sorbitol, polyethylene glycols, lactilol, xylitol, and the like thickening agents, such as certain silica used for this purpose (Tixosil 43®, sold by Rhône-Poulenc, and the like) and/or polymers, used alone or in combination, such as xanthan gum, guar gum, cellulose derivatives (carboxymethylcellulose, hydroxyethylcellulose, hydroxypropylcellulose, hydroxypropylmethylcellulose, and the like), crosslinked polyacrylates, such as Carbopol® products distributed by Goodrich, alginates or carrageenans, Viscarin®, and the like, polishing abrasives, such as certain silicas, precipitated calcium carbonate, magnesium carbonate, calcium phosphates, titanium, zinc or tin oxides, talc, kaolin, and the like, bactericidal, antimicrobial or anti-plaque therapeutic agents, such as zinc citrate, polyphosphates, guanidines, bisbiguanides or other therapeutic cationic organic compound, flavoring agents (essence of aniseed, of Chinese anise, of mint, of juniper, cinnamon, clove or rose), sweeteners, colorants (chlorophyll), preservatives, and the like.

The following example is given by way of illustration.

EXAMPLE

Starting materials used:

base surface-active agent (BSA)

SDS: sodium dodecyl sulfate, sold by Fluka $C_{14}$TAB: tetradecyltrimethylammonium bromide, sold by Aldrich BSAF: surface-active formulation comprising
  21% by weight, on a dry basis, of sodium lauryl ether sulfate (Empicol ESB/3M, sold by Albright & Wilson)
  3% by weight, on a dry basis, of ethoxylated alcohol comprising an average of 6 oxyethylene units (Rhodasurf IDO60, sold by Rhône-Poulenc)
  3% by weight, on a dry basis, of cocoamidopropyl betaine (Dehyton K, sold by Henkel)
  q.s. for 100% by weight of water with adjustment to pH 7, grease (G)

50/50 by weight mixture of sunflower oil and of margarine additive (ADD)

Forafac 1110 D, ethoxylated polyfluoroalcohol sold by Elf Atochem

Forafac 1157, perfluoroalkyl betaine sold by Elf Atochem

Forafac 1179, polyfluoroalkylammonium salt sold by Elf Atochem

Zonyl FSK, of formula $F(CF_2CF_2)_{3-8}CH_2CH(OCOCH_3)CH_2N^+(CH_3)_2CH_2CH_2CO_2^-$ sold by Pont de Nemours.

The performances of the additives (ADD) as foam-stabilizing agents are tested according to the following procedure:

250 ml of an aqueous solution comprising 0.4% by weight of surface-active agent or surface-active formulation SDS, $C_{14}$TAB or BSAF are prepared.

1) The solution is introduced into a 2 liter beaker comprising an anchor stirrer half-immersed in the said solution.

The solution is stirred at 400 revolutions/minute for 1 minute.

The foam height FH is measured.

2) The operation 1) described above is repeated, 10 ml of grease (G) being added to the solution of (BSA).

The medium is stirred at 400 revolutions/minute for 1 minute.

The foam height GFH is measured.

3) The operation 1) described above is repeated, 10 ml of grease (G) and 0.1% by weight of additive (ADD) being added to the solution of (BSA).

The medium is stirred at 400 revolutions/minute for 1 minute.

The foam height AGFH is measured.

The performance of the additive (ADD) tested is expressed by the ratio $$P\% = [(AGFH - GFH)/GFH] \times 100$$

The results obtained appear in Table 1.

This table also displays, for solutions comprising 0.4% of SDS and of $C_{14}$TAB as base surface-active agents (BSA), the values of water/air surface tension
  $\gamma_{water/air}$ without additive
  $\gamma_{(ADD)\ water/air}$ in the presence of additive (ADD) (0.1%)

grease/water interfacial tension
  $\gamma_1$ without additive
  $\gamma_2$ in the presence of additive (ADD) (0.1%)

The water/grease interfacial tension measurements are carried out according to the drop volume method described in the work by Adamson A. W. "Physical Chemistry of Surfaces", 2nd edition, Interscience, New York, 1967.

Those of surface tension are carried out using a Lauda® TVTI surface tension meter.

It is found that:

the surface tensions $\gamma_{(ADD)\ water/air}$ of the aqueous solutions comprising 0.1% of additive (ADD) are less than 22 mN/m.

the addition of additive (ADD) to the aqueous solution of base surface-active agent (BSA) does not modify by more than 0.4 mN/m the grease/aqueous solution of base surface-active agent (BSA) interfacial tension.

TABLE 1

| ADDITIVE (ADD) | Base surfactant (BSA) | | |
| --- | --- | --- | --- |
|  | SDS | $C_{14}$TAB | BSAF |
| none |  |  |  |
| FH (mm) | 110 | 95 | 85 |
| GFH (mm) | 17 | 17 | 4 |
| $\gamma_{water/air}$ (mN/m) | 38.1 | 38.5 |  |

TABLE 1-continued

| ADDITIVE (ADD) | Base surfactant (BSA) | | |
|---|---|---|---|
|  | SDS | $C_{14}TAB$ | BSAF |
| $\gamma_1$ (mN/m) | 6.3 | 9 | |
| Forafac 1110D | | | |
| AGFH mm | 25 | 40 | 13 |
| P % | 47% | 135% | 225% |
| $\gamma_{(ADD)water/air}$ (mN/m) | 18.3 | 18.1 | |
| $\gamma_2$ (mN/m) | 6.5 | 9 | |
| $|\gamma_1-\gamma_2|$ (mN/m) | 0.2 | 0 | |
| Forafac 1157 | | | |
| AGFH mm | 50 | 60 | 23 |
| P % | 194% | 253% | 475% |
| $\gamma_{(ADD)water/air}$ (mN/m) | 16.4 | 15.8 | |
| $\gamma_2$ (mN/m) | 5.9 | 8.6 | |
| $|\gamma_1-\gamma_2|$ (mN/m) | 0.4 | 0.4 | |
| Forafac 1179 | | | |
| AGFH mm | 25 | 75 | 5 |
| P % | 47% | 341% | 25% |
| Zonyl FSK | | | |
| AGFH mm | 36 | 65 | |
| P % | 112% | 282% | |

What is claimed is:

1. A liquid detergent composition for washing dishes by hand or textiles by hand comprising an effective amount of a foaming aqueous medium (FAM) which can form stable foams in the presence of grease (G), said foaming aqueous medium (FAM) comprising water and at least one base surface-active agent (BSA) which can disperse and/or dissolve the grease (G) in the water and which comprises at least one amphiphilic additive (ADD) compatible with said base surface-active agent (BSA), said amphiphilic additive (ADD) exhibiting, at a concentration of 0.1% by weight in water, a surface tension $\gamma_{(ADD)\,water/air}$ of less than 25 mN/m at 25° C. and exhibiting an affinity for the grease (G) which is less than that of the base surface-active agent (BSA) for said grease (G), wherein said amphiphilic additive (ADD) comprises surface-active agents of the formula
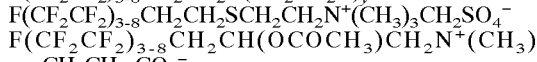

perfluoroalkyl betaines,
ethoxylated polyfluoroalcohols
polyfluoroalkyl ammonium salts
surface-active agents, the hydrophilic part of which comprises one or more saccharide unit(s) comprising from 5 to 6 carbon atoms and the hydrophobic part of which comprises a unit of formula $R_F(CH2)n^-$, where n can range from 2 to 20, and $R_F$ represents a perfluoroalkyl unit of formula $C_mF2_{m+1}$ with m being able to range from 1 to 10, polyacrylates exhibiting $R_F(CH_2)_n-$ groups, where n can range from 2 to 20, and $R_F$ represents a perfluoroalkyl unit of formula $C_mF_{2m+1}$ with m being able to range from 1 to 10.

2. A liquid composition for body hygiene or oral hygiene comprising an effective amount of a foaming aqueous medium (FAM) which can form stable foams in the presence of grease (G), said foaming aqueous medium (FAM) comprising water and at least one base surface-active agent (BSA) which can disperse and/or dissolve the grease (G) in the water and which comprises at least one amphiphilic additive (ADD) compatible with said base surface-active agent (BSA), wherein the (ADD)/(BSA) ratio by weight, each of these two being expressed on a dry basis, being on the order of 0.5/100 to 40/100, said amphiphilic additive (ADD) exhibiting, at a concentration of 0.1 % by weight in water, a surface tension $\gamma_{(ADD)\,water/air}$ of less than 25 mN/m at 25° C. and exhibiting an affinity for the grease (G) which is less than that of the base surface-active agent (BSA) for said grease (G), wherein said amphiphilic additive (ADD) comprises surface-active agents of the formula
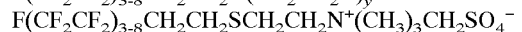
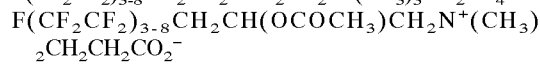

perfluoroalkyl betaines,
ethoxylated polyfluoroalcohols
polyfluoroalkyl ammonium salts
surface-active agents, the hydrophilic part of which comprises one or more saccharide unit(s) comprising from 5 to 6 carbon atoms and the hydrophobic part of which comprises a unit of formula $R_F(CH2)n^-$, where n can range from 2 to 20, and $R_F$ represents a perfluoroalkyl unit of formula $C_mF2_{m+1}$ with m being able to range from 1 to 10, polyacrylates exhibiting $R_F(CH_2)_n-$ groups, where n can range from 2 to 20, and $R_F$ represents a perfluoroalkyl unit of formula $C_mF_{2m+1}$ with m being able to range from 1 to 10.

* * * * *